(12) United States Patent
Fritsch et al.

(10) Patent No.: US 9,989,452 B2
(45) Date of Patent: Jun. 5, 2018

(54) MAGNETOHYDRODYNAMIC MICROFLUIDIC SYSTEMS INCLUDING MODIFIED ELECTRODES AND METHODS OF USING THE SAME

(71) Applicant: BOARD OF TRUSTEES OF THE UNIVERSITY OF ARKANSAS, Little Rock, AR (US)

(72) Inventors: Ingrid Fritsch, Fayetteville, AR (US); Christena Nash, Roswell, GA (US); Sai Kumar, Johns Creek, GA (US); Timothy Muldoon, Fayetteville, AR (US); Kartik Balachandran, Fayetteville, AR (US); Adair Claycomb, Arlington, TX (US); Matthew D. Gerner, Fayetteville, AR (US); Joshua Hutcheson, Fayetteville, AR (US); Foysal Z. Khan, Fayetteville, AR (US); Amy Powless, Rogers, AR (US); Sandra Prieto, Siloam Springs, AR (US); Preston G. Scrape, Jonesboro, AR (US); Melissa C. Weston, Duncan, OK (US)

(*) Notice: Subject to any disclaimer, the term of this patent is extended or adjusted under 35 U.S.C. 154(b) by 266 days.

(21) Appl. No.: 14/951,322

(22) Filed: Nov. 24, 2015

(65) Prior Publication Data
US 2016/0146756 A1    May 26, 2016

Related U.S. Application Data

(60) Provisional application No. 62/084,466, filed on Nov. 25, 2014, provisional application No. 62/152,117, filed on Apr. 24, 2015.

(51) Int. Cl.
*G01N 27/26* (2006.01)
*G01N 15/14* (2006.01)
(Continued)

(52) U.S. Cl.
CPC ..... *G01N 15/1475* (2013.01); *B01F 13/0077* (2013.01); *B01L 3/50273* (2013.01);
(Continued)

(58) Field of Classification Search
None
See application file for complete search history.

(56) References Cited

U.S. PATENT DOCUMENTS

2008/0241910 A1* 10/2008 Jung ............... G01N 33/54326
435/287.1

OTHER PUBLICATIONS

Fritsch_Electrochemistry, Magnetic Fields, and Fluid Flow: Programming the Next Generation of Microfluidics; University of Arkansas; Presentation—Brigham Young University; 51 pages; no month, 2016.

Hutchenson et al; A light sheet confocal microscope for image cytometry with a variable linear slit detector; Research Gate; High-Speel Biomedical Imaging and Spectroscopy; Conference Paper, 7 pages; SPIE; vol. 9720, 97200U; no month, 2015.

(Continued)

*Primary Examiner* — Arun S Phasge
(74) *Attorney, Agent, or Firm* — Keith A Vogt; Vogt IP

(57) ABSTRACT

A magnetohydrodynamic microfluidic system and a method of pumping a fluid using a magnetohydrodynamic system are disclosed. The method includes applying at least one of an electric current and an electric voltage to a first modified electrode and a second electrode to generate an ionic current between the first modified electrode and the second electrode and to cause a current carrying species to move to or from the modified electrode, applying a magnetic field perpendicular to an ionic current vector, the magnetic field and the ionic current combining to induce flow of the fluid in a direction perpendicular to the magnetic field and the ionic current vector, and maintaining fluid flow by recharging the modified electrode.

22 Claims, 11 Drawing Sheets

(51) Int. Cl.
- *B01L 3/00* (2006.01)
- *F04B 19/00* (2006.01)
- *B01F 13/00* (2006.01)
- *G01N 15/00* (2006.01)
- *G01N 27/447* (2006.01)

(52) U.S. Cl.
CPC ...... *B01L 3/502761* (2013.01); *F04B 19/006* (2013.01); *G01N 15/147* (2013.01); *B01L 2200/0647* (2013.01); *B01L 2300/0654* (2013.01); *B01L 2300/0816* (2013.01); *B01L 2400/043* (2013.01); *B01L 2400/0415* (2013.01); *G01N 27/447* (2013.01); *G01N 2015/008* (2013.01); *G01N 2015/1486* (2013.01)

(56) References Cited

OTHER PUBLICATIONS

Hutchenson et al; A widefield fluorescence microscope with a linear image sensor for image cytometry of biospecimens: Considerations for image quality optimization; Review of Scientific Instruments; Sep. 2015; 9 pages; AIP Publishing.

Khan et al; Studies Toward Lab-on-a-Chip Separations and Detection Using Redox Magnetohydrodynamic icrofluidics; Abstract; 2 pages; Apr. 27, 2016; http://,a.ecsdl.org/content/MA2015-01/2227.abstract.

Nash et al; Poly(3,4-ethylenedioxythiophene)-Modified Electrodes for Microfluidics Pumping with Redox-Magnetohydrodynamics: Improving Compatibility for Broader Applciation syb Eliminating Addition of Redox species to Solution; Analytical Chemistry; Dec. 3, 2015; ACS Publications; 9 pages.

* cited by examiner

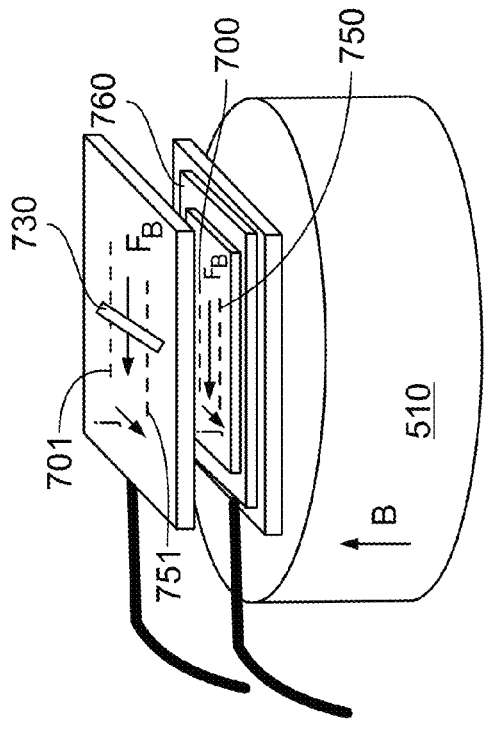
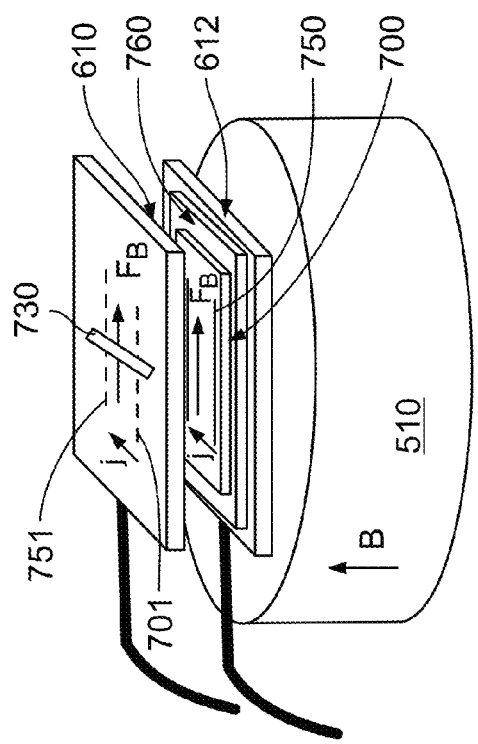
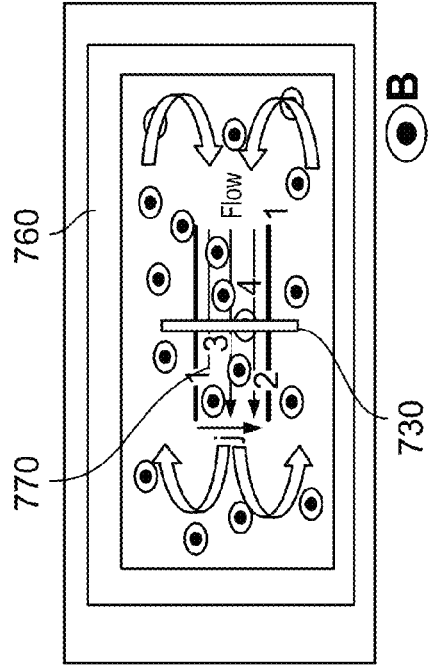
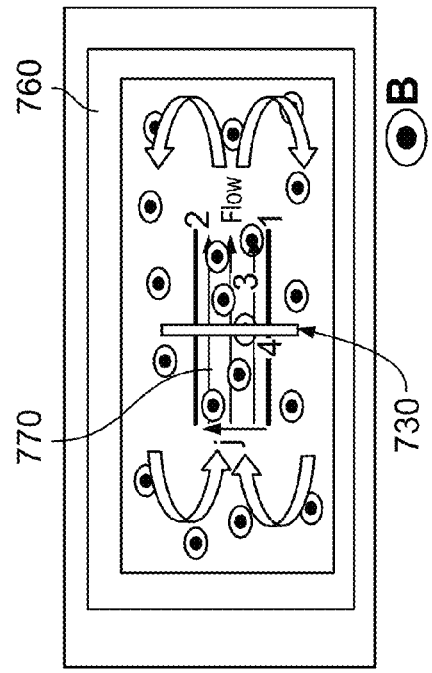
FIG. 13A
FIG. 13B
FIG. 13C
FIG. 13D

MAGNETOHYDRODYNAMIC MICROFLUIDIC SYSTEMS INCLUDING MODIFIED ELECTRODES AND METHODS OF USING THE SAME

RELATED APPLICATIONS

This application claims the benefit of U.S. Provisional Application No. 62/084,466 filed on Nov. 25, 2014 and U.S. Provisional Application No. 62/152,117 filed on Apr. 24, 2015, both of which are herein incorporated by reference.

STATEMENT REGARDING FEDERALLY SPONSORED RESEARCH & DEVELOPMENT

This invention was made with government support under NSF CHE0719097 and NSF CBET1336853 awarded by the NSF. The government has certain rights in the invention.

INCORPORATION BY REFERENCE OF MATERIAL SUBMITTED ON A COMPACT DISC

Not applicable.

BACKGROUND OF THE INVENTION

The present invention is directed to, among other things, the miniaturization of analytical techniques from a full lab or bench top scale to a lab-on-a-chip (LOAC) device which promises to improve portability, power consumption, reagent and waste volumes, automation, and analysis time. LOAC devices show promise for revolutionizing analysis needed in medical diagnosis, environmental field studies, genomic studies, and for performing synthetic reactions. One of the aspects of LOAC applications is the microfluidics, i.e., the manipulation of small amounts of fluid within the device.

In magnetohydrodynamics (MHD), the magnetohydrodynamic force, $F_B$ (N·m$^{-3}$), which results in fluid flow, is generated by ionic current (normalized to the cross sectional area through which it passes), j (C·s$^{-1}$·m$^{-2}$), and a magnetic field, B (T) that is perpendicular to the ionic current vector, j. The magnitude and direction of $F_B$ follows the right-hand rule according to the cross-product relationship, $F_B = j \times B$.

One of the first approaches that used MHD to pump solutions for microfluidics used direct current (DC) applied to electrodes on either side of a channel filled with electrolyte in the presence of a uniform magnetic field generated from a permanent magnet. This method, when applied to aqueous solutions corroded electrodes and produced bubbles from the electrolysis of water, which interrupted fluid flow.

Two methods have been used to alleviate the problem of water electrolysis and electrode degradation during MHD microfluidics: (1) the addition of redox species to solution, and (2) application of a sinusoidal potential or current waveform to the electrodes.

In the first method, the addition of redox species to the solution allowed pumping at low voltages while keeping the current high to achieve high fluid velocities. The maximum achievable current was proportional to the concentration of redox species; therefore, the higher the concentration, the higher the fluid velocities. However, the introduction of redox species raises concerns about the risk of contamination and interference with analyte detection and with the biocompatibility of the pumping system. Low concentrations of redox species have been shown to be compatible with heart tissue and with alkaline phosphatase, an enzyme commonly used in immunoassay applications. However, the use of low concentrations limits the highest possible velocities that can be achieved.

In the second method, bubble generation was minimized by application of a sinusoidal potential or current waveform at the electrodes while simultaneously altering the magnetic field direction. This approach is called AC-MHD. In one AC-MHD study, a sinusoidal electric current of a frequency greater than 1 kHz was passed through an electrolytic solution to prevent bubble generation and electrode degradation. Higher currents, and therefore higher velocities, were possible at the higher frequencies before bubble formation became a problem, but the magnetic field dropped significantly at frequencies above 1 kHz.

Thus, there is a need for a microfluidic system that is able to pump fluid between two locations, easily reverse fluid flow direction, adjust fluid flow velocity, trap species within a certain volume, mix solutions of different composition, and split off a fluid volume for further handling.

In other aspects, the present invention is directed to, among other things, improving traditional methods for neutrophil counting and three-part differentials (counting granulocyte, lymphocyte, and monocyte sub-populations of leukocytes) that typically rely on automated methods which use blood drawn via venipuncture. Three-part differential tests are essential in monitoring leukopenia in patients receiving chemotherapy. Chemotherapy typically leaves the patient myelosuppressed and susceptible to treatment-induced infection. The differential test is also used to monitor the body's response to latent infections and predict other potential hematopoietic disorders. A point-of-care (POC) hematology device is desirable to provide differential counts to improve the speed at which results are delivered with the same or improved accuracy of traditional flow cytometry or Coulter counting methods, while greatly reducing cost.

A challenge for oncologists and chemotherapy patients is treatment-induced myelosuppression. Monitoring and diagnosing this effect requires multiple draws by painful venipuncture and expensive non-portable hematology analyzers; which themselves require multiple reagents for analysis and a trained lab technician for operation. These limitations restrict the ability to diagnose and monitor myelosuppression at the point-of-care and in low-resource settings.

Since POC systems provide rapid assessment of easily obtained biological samples, such as blood, they are ideally suited for low-resource settings. Although these approaches have many benefits, additional reductions in cost are necessary since many POC diagnostic systems rely on reagents that are difficult and expensive to produce, store and package effectively.

Optical imaging techniques, such as optofluidics, the combination of microfluidics technology and optics, and computer-aided diagnostics also have great promise to reduce the cost of individual screening tests.

Proflavine, an acridine-derived dye, is a small molecule with a high quantum yield (~35%) of fluorescence. It has previously been used in numerous imaging studies of intact tissue. Proflavine is able to cross cell membranes and preferentially intercalate DNA; more notably, it poorly stains other intracellular structures. This preferential intranuclear staining mechanism makes it an attractive dye for a point-of-care three-part differential due to the fact that leukocytes are the only nucleated cells in whole blood. This unique quality eliminates the need to lyse or remove the red blood cells, as other extant methods require. The dye may be applied to whole blood samples without the need for special environmental controls or lengthy incubation steps, buffers, detergents, or ligand-targeting moieties. This makes it ideal for a point-of-care and avoids long processing times.

In yet other aspects, the present invention is directed to, among other things, addressing the need for high-throughput cell characterization systems capable of morphological characterization of large numbers of living cells in a diverse range of environments, from in vitro cell culture to agricultural applications to biological specimens. There is significant interest in sensing molecular, metabolic, and morphological changes between different cell populations present in a sample or in response to chemotherapeutic interventions; These research areas may encompass basic cell biology, tumorigenesis, drug discovery, and a broad array of other disciplines. Conventional flow cytometry systems require significant investment and have limited portability, and are generally limited to exogenous targeting of cellular proteins, requiring a priori knowledge of the target of interest. Optofluidics devices, particularly those coupled to smartphones, have demonstrated excellent portability and show great promise for point of care diagnostic use, but still require the use of pressure-driven bulky syringe pumps, translation stages, and other methods for specimen handling.

Vital clinical applications, such as detection of extremely rare cells in heterogeneous samples, such as circulating tumor cells or cells with intracellular parasites, such as in malaria, make conventional microscopy of a small number of cells unreliable due to under-sampling bias and the need to screen vast numbers of high power fields. Conventional flow cytometry methods are able to screen large numbers of cells but are generally insensitive to intrinsic morphologic or metabolic changes within individual cells, in addition to the lack of portability of these devices.

Commercial imaging cytometry systems currently exist, primarily for research based applications, although some automated methods are available in hematopathology departments in tertiary care centers in the United States. These systems typically acquire data on moderately large numbers of cells, up to one 96-well plate over ten minutes in stationary applications or several tens of microliters for cell suspensions. However, like flow cytometry systems, these are typically limited in scope and insensitive to endogenous reporters of metabolism, such as intrinsic nicotinamide adenine dinucleotide (NADH) or flavin adenine dinucleotide (FAD) fluorescence. Furthermore, due to conventional imaging approaches utilizing complex scanning mirrors and photomultiplier tubes, these systems are generally unsuitable for low-power, and portable operation.

In still further aspects, the present invention is directed to, among other things, addressing ways to scan a sample containing cells. One way is to stain cells on a slide and move the slide beneath the viewing device. This is not an automated approach and requires several steps and skill to handle the sample and perform the staining. A more automated approach is to program the transfer of a sample through the use of microfluidics. Mechanical and electrokinetic pumping are possible options to perform this function.

Electrokinetic pumping has a flat profile that avoids the need to compensate for varied fluid flow across a horizontal plane, but is restricted to narrow channels and is highly dependent on the physicochemical properties of the sidewalls (fluid velocity will change depending on the solution properties). Mechanical pumping, such as the use of syringe pumps, requires equipment exterior to the viewing device, moving parts, adds bulk and channels to direct fluid flow, and produces a non-uniform, parabolic flow profile.

Magnetohydrodynamic (MHD) fluid transport is a unique pumping approach that is compatible with a broad range of device shapes and dimensions, does not require moving parts, and provides highly tunable flow patterns and speeds without valves. This pumping approach downsizes, simplifies, and extends the function of the viewing method. MHD offers the flexibility of bidirectional pumping as well as pumping in a circular path. Notably, the entire fluidic manipulation occurs within a microfluidic chip, without necessitating the use of valves and external micropumps. MHD is also compatible with both aqueous and non-aqueous solutions which allows this technique to perform in synthetic organic and biological applications.

As set forth below, the embodiments of the present invention overcome the above described shortcomings in the prior art and provide other advantages.

BRIEF SUMMARY OF THE INVENTION

In one aspect, the present invention features a method of pumping a fluid, the method including applying at least one of an electric current and an electric voltage between a first modified electrode and a second electrode to generate an ionic current between the first modified electrode and the second electrode and to cause a current carrying species to move to or from the modified electrode, and applying a magnetic field perpendicular to an ionic current vector (j) of the ionic current, the magnetic field and the ionic current combining to induce flow of the fluid.

In one embodiment, the method further includes maintaining fluid flow by recharging the modified electrode. In some embodiments, the recharging includes applying at least one of a varying voltage and a varying current to the electrodes, and applying a varying magnetic field. In one embodiment, applying the at least one of a varying voltage and a varying current to the electrodes and applying the varying magnetic field occur in synchrony.

In another embodiment, the method further includes applying at least one of a sinusoidal potential, a current waveform, and a step function to the electrodes while simultaneously altering the direction of the magnetic field. In another embodiment, the present invention uses a predetermined waveform such as saw tooth, exponential decays, bizarre linear combinations, linear, non-linear and combinations thereof.

In some embodiments, the method further includes intermittently recharging the modified electrodes. In one embodiment, the intermittent recharging includes directing the flow of ionic current such that an ionic current vector, j, is in parallel with the magnetic field. In other embodiments, the flow of ionic current is directed such that the ionic current vector, j, is in parallel with the magnetic field and does not alter the magnetic field. In other embodiments, intermittently recharging the modified electrodes includes directing the magnetohydrodynamic force such that the absolute value of the magnetohydrodynamic force is greater than zero.

In one embodiment, the fluid flow during recharging of the modified electrode is approximately zero. In another embodiment, the fluid flow is a pulsed fluid flow during recharging.

In some embodiments, the recharging includes applying at least one of a varying voltage and a varying current to the electrodes, and changing the direction of the magnetic field.

In some embodiments, the magnetic field and the ionic current combine to produce at least one of a rotational flow of the fluid or a spiral flow of the fluid.

In another aspect, the present invention features a microfluidic system that includes at least two electrodes, a first of the at least two electrodes comprising a modified electrode comprising an immobilized electroactive chemical species, an ionic current passing between the at least two electrodes, a magnetic field perpendicular to an ionic current vector of the ionic current, and a fluid. In one embodiment, the system further includes at least one microfluidic channel. In some embodiments, a second of the at least two electrodes includes a modified electrode comprising an immobilized electroactive chemical species.

In another embodiment, the system further includes a cell defined by at least two opposing surfaces, the first and second electrodes being parallel to one another, the first electrode being positioned on a surface of the cell opposite the second electrode.

In other embodiments, the first and second electrodes are concentric with one another. In another embodiment, the first and second electrodes are concentric and coplanar with one another.

In some embodiments, the system further includes a cell defined by at least two opposing surfaces, and wherein the first and second electrodes are concentric with one another, each of the first and second electrodes is in a form including at least one of a disk and a ring, the first electrode being positioned on a first surface of the cell, and the second electrode being positioned on a second surface of the cell opposite the first surface.

In another embodiment, the system further includes a microfluidic channel defined by at least a first side wall and a second side wall.

In other embodiments, the magnetic field and the ionic current combine to produce at least one of a rotational flow of the fluid and a spiral flow of the fluid.

In other embodiments, the present invention features a microfluidic system that exhibits the ability to control fluid flow and the ability to sustain fluid flow in a microfluidic system through magnetohydrodynamics and modified electrodes.

In other embodiments, the present invention features a microfluidic system in which modified electrodes can be intermittently recharged in a magnetic field or alternatingly recharged in a synchronized magnetic field.

In other embodiments, the present invention combines optofluidics and staining of leukocytes in whole blood to provide a low-cost point of care screening tool for myelosuppresion or infection.

In other embodiments, the optofluidics system of the present invention consists of an area scanning fluorescence microscope and a microfluidics channel that may be made with poly(dimethylsiloxane) (PDMS) and grafted by soft-film photolithography.

In other embodiments, the present invention provides a method to stain leukocytes in whole blood from a finger prick. The whole blood flows through the microfluidics channel as a 455 nm LED excites proflavine stained leukocytes emitting a fluorescent signal. The CMOS sensor on the microscope detects the signal to form an image. The image is then processed post-acquisition using a classification algorithm to detect and differentiate minute variations in cell morphologic features to build a three-part differential by texture analysis.

In other embodiments, the present invention, following the collection of whole blood samples and vital staining with proflavine, provides a PDMS-based capillary channel that sequentially deliver cells to the focal plane of the sensor with precise fluid control.

In addition, in other embodiments, the present invention provides a system that further uses computer-aided diagnostics for detection and classification of minute distinctions in cellular morphologic features. The morphologic features may be classified by analysis of spatial frequency or via a gray level co-occurrence matrix (GLCM) that analyzes the degree of disparity or randomness in the image.

In other embodiments, the present invention uses other imaging methods to decrease the overall cost of the system including using a Raspberry Pi microprocessor as an alternative to a desktop or laptop computer. In yet other embodiments, the present invention is a fully attachable to a cell phone unit that will increase portability and accessibility.

By using the above described subsystems, the present invention provides a new point-of-care diagnostic tool for low-resource, rural settings and rapid diagnostics.

In other embodiments, the present invention provides methods and devices that reduce or eliminate the need to add redox species to the solution. The present invention, in one an alternative approach, is compatible with both DC and AC-MHD fluidics immobilizing the redox species at the electrode surface. Redox species can be immobilized at the electrode surface in a variety of ways and in a variety of forms. Immobilization allows minimal interaction with analytes in solution and, at the same time, offers higher coulombic capacity than is possible with solution species alone.

One kind of immobilized redox material and method is using conducting polymers on the electrodes which may be applied by electrochemical deposition. Using conducting polymers on the electrodes provides an accessible charge (low resistance) and a large faradic current that produces high j values and therefore a larger body force ($F_B$) and faster fluid flow. Many conducting polymers are susceptible to oxidation and reduction reaction, have delocalized conjugated $\pi$ systems, low ionization potentials, and high electron affinities which make them suitable as immobilized redox species with high conductivity.

Other desirable properties of immobilized redox materials and matrices on the electrodes include reproducibility, controlled film thickness on well-defined electrodes, and simplicity. Some examples of conducting polymers are polyacetylene, polyphenylenes, polypyrrole, polyaniline, polyazines, polythiophenes, and their derivatives. PEDOT ((Poly 3, 4-ethylenedioxythiophene) has been used as a working example for the present invention since these films have a fast response and high coulombic capacity (stored charge), a reversible doping state, excellent chemical and thermal stability, low band gap, pH independency, and low redox potential.

In other aspects, other embodiments of the present invention concern an imaging cytometry device which utilizes MHD fluid transport and a high resolution linear imaging microscope. The merging of magnetohydrodynamic (MHD) fluid transport technology, imaging with a light sheet confocal microscope, and a linear sensor presents an innovative method to expand the role of flow cytometry and imaging cytometry applications to cell biology. This will enable the use of these methods in educational settings, and significantly amplify the impact of optical imaging devices for point of care diagnostics in low-resource settings. By coupling these technologies, in certain embodiments, the present invention provides a confocal microscopy platform with no moving parts capable of continuous high spatiotemporal resolution imaging of cytology specimens. This unique approach has the potential to be transformative across a broad range of biomedical applications.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

In the drawings, which are not necessarily drawn to scale, like numerals may describe substantially similar components throughout the several views. Like numerals having different letter suffixes may represent different instances of substantially similar components. The drawings illustrate generally, by way of example, but not by way of limitation, a detailed description of certain embodiments discussed in the present document.

FIGS. 13A and 13B illustrate an embodiment of a rechargeable MHD microfluidic system that may be used with the embodiment shown in FIG. 11.

FIGS. 13C and 13D illustrates how the direction of the fluid flow may be reversed in the embodiment shown in FIGS. 13A and 13B.

DETAILED DESCRIPTION OF THE INVENTION

Detailed embodiments of the present invention are disclosed herein; however, it is to be understood that the disclosed embodiments are merely exemplars of the invention, which may be embodied in various forms. Therefore, specific structural and functional details disclosed herein are not to be interpreted as limiting, but merely as a representative basis for teaching one skilled in the art to variously employ the present invention in virtually any appropriately detailed method, structure or system. Further, the terms and phrases used herein are not intended to be limiting, but rather to provide an understandable description of the invention.

The magnetohydrodynamics (MHD) microfluidic system of the present invention is useful for pumping fluid that includes a current carrying species. The MHD microfluidic system includes an electromagnet that generates a magnetic field, at least two electrodes, at least one of which may be a modified electrode, a cell, an electric field generator, a function generator, and a fluid disposed in the cell. The fluid includes a current carrying species. The first and second electrodes and the fluid are arranged such that applying an electric voltage or an electric current to at least one of the electrodes causes an ionic current to flow between the electrodes. The electromagnet is arranged relative to the electrodes such that the magnetic field is perpendicular to the ionic current vector, j.

Figure 1A:
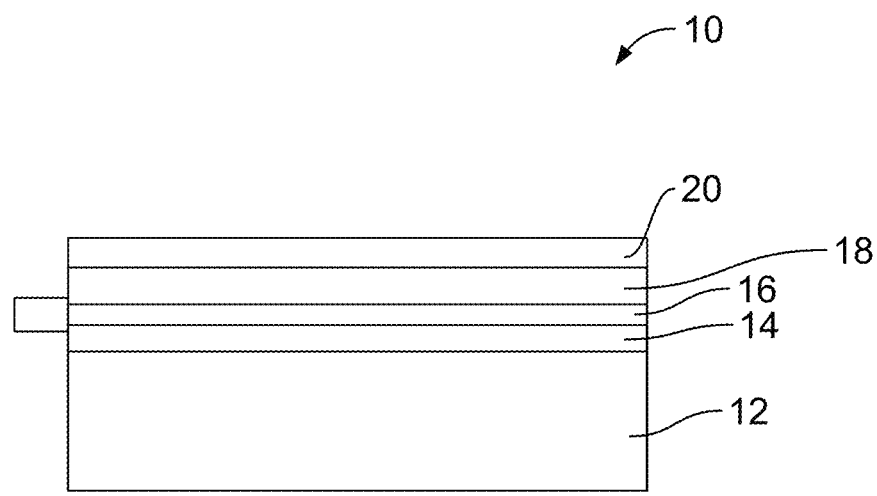
FIG. 1A is a side view of a magnetohydrodynamic (MHD) microfluidic system according to one embodiment of the present invention.
Figure 1B:
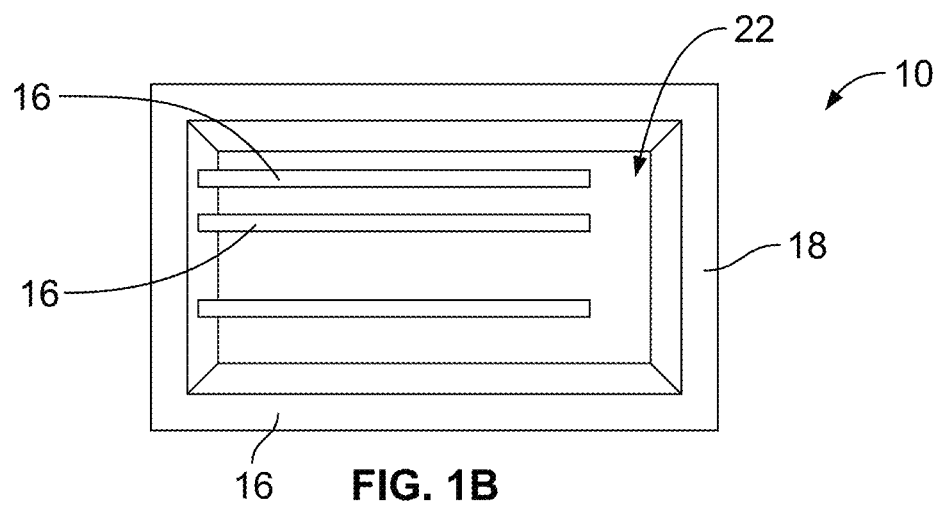
FIG. 1B is a top view of the MHD of FIG. 1A with the top wall 20 removed exposing the electrodes and side walls of a cell defined by the gasket.

In one embodiment, the MHD microfluidic system 10 includes an electromagnet 12, silicon chip 14, an array of electrodes 16 disposed on the chip 14, gasket 18, and a glass slide 20, as illustrated in FIG. 1A. Gasket 18 defines the side walls of cell 22. Chip 14 provides the bottom wall of cell 22 and glass slide 20 provides the top wall of the cell. As shown in FIG. 1B, top wall 20 of the system includes electrodes 16 that are positioned within cell walls 22 as defined by the gasket 18.

In operation, an electric current or an electric voltage is applied between the first and second electrodes to generate an ionic current between the first electrode and the second electrode, a magnetic field is applied perpendicular to the ionic current vector, j, and the magnetic field and the ionic current combine to induce flow of the fluid in a direction that is perpendicular to both the magnetic field and the ionic current vector, j. Pumping may be sustained over long periods of time by altering the ionic current, the magnetic field, and combinations thereof, to allow the electrodes to recharge without completely reversing the fluid flow as described in more detail below. It is to be understood that the relationship of the magnetic field vector, B, and the ionic current vector j can be perpendicular or substantially perpendicular to one another in one location while exhibiting another relationship in another location. In other words, a portion of the magnetic field can be perpendicular to a portion of the electrical field created by the ionic current while another portion of the magnetic field is not perpendicular to another portion of the electrical field created by the ionic current.

The pumping can also achieve a variety of suitable flow patterns including, e.g., linear, rotational, and spiral fluid flow patterns.

Figure 2A:
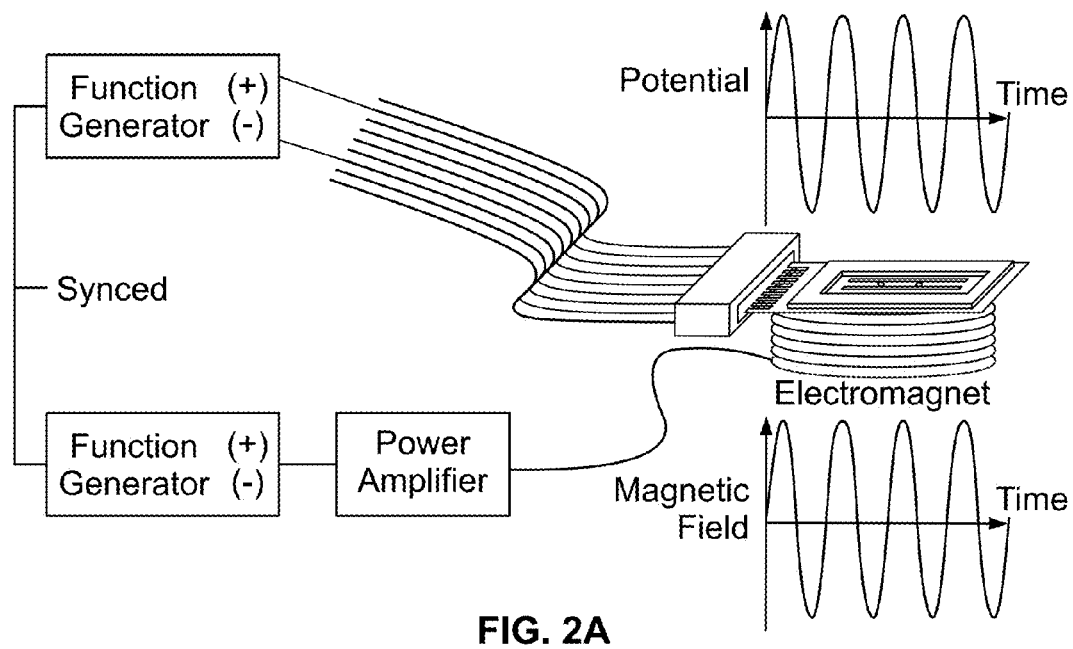
FIG. 2A is a block diagram for the electronics of a magnetohydrodynamic microfluidic system according to another embodiment of the invention.
Figure 2B:
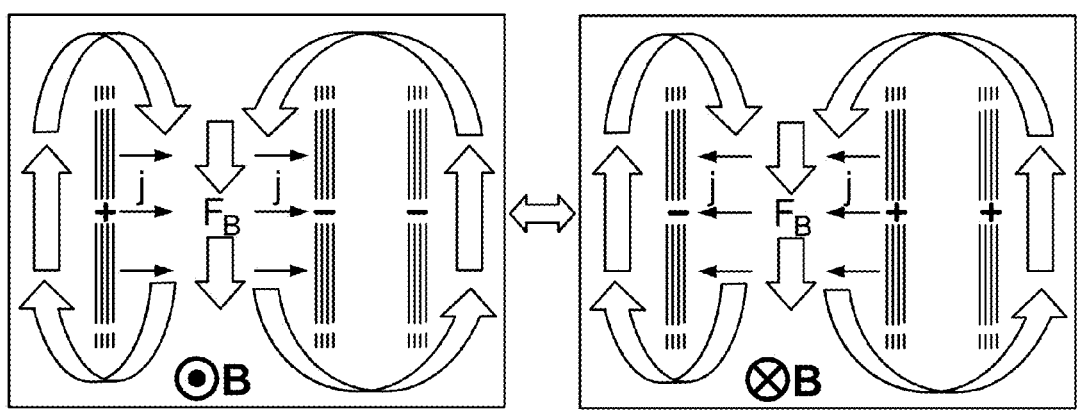
FIG. 2B is an illustration of the vectors reflecting the magnetic field (B), ionic current (j) and fluid flow ($F_B$) in the system of FIG. 2A, when the electrical and magnetic fields are synchronized to maintain fluid flow.

FIG. 2A illustrates an embodiment of the MHD microfluidic system in which a first function generator is coupled to sets of modified microband electrodes, and a second function generator is coupled to the electromagnet through a power amplifier. There are three sets of modified microband electrodes (e.g., PEDOT-modified gold band electrodes): set 1 is the working electrode, and sets 2 and 3 are the combined auxiliary/quasi-reference active electrodes. Set 1 electrodes are oppositely biased from sets 2 and 3. During operation, the first functional generator applies a sinusoidal potential (which is also known as a current waveform) to the electrodes, which produces an AC current, and the second functional generator simultaneously applies a sinusoidal potential to the electromagnet producing an AC magnetic field. The sinusoidal waveforms applied to the electrodes and the magnet are synchronized. FIG. 2B is an illustration of the vectors reflecting the magnetic field (B), ionic current (j) and fluid flow ($F_B$) in the system of FIG. 2A, when the electrical and magnetic fields are synchronized to maintain fluid flow.

Figure 3A:
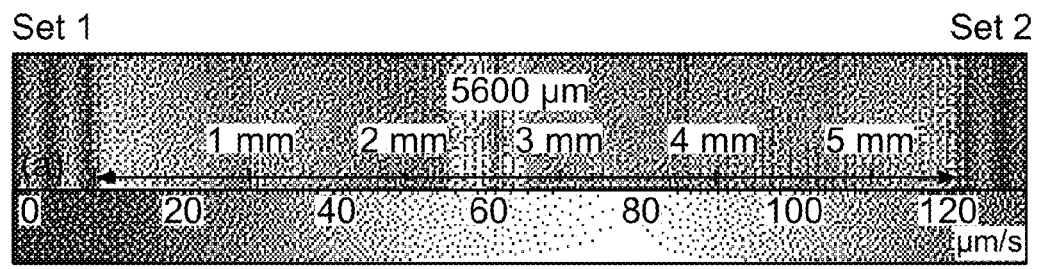
FIG. 3A is a PIV images illustrating flow profile in the 5600 μm gap between 3,4-dioxyethylenethiophene polymer (PEDOT)-modified microband electrodes.
Figure 3B:
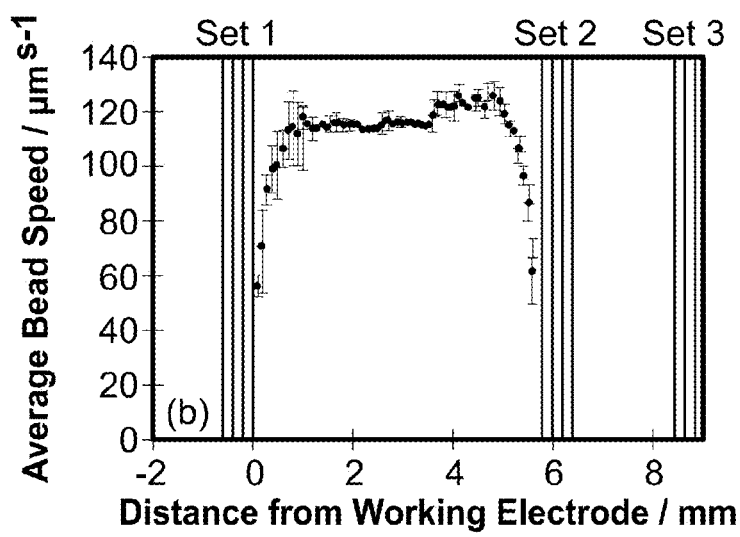
FIG. 3B is a plot of the average bead velocity ($\mu m \cdot s^{-1}$) versus distance (in mm) from working electrodes. Error bars are the standard deviation for each of the data points.

Particle image velocimetry (PIV) analysis of the flow profile in the 5600 μm gap between two PEDOT-modified microband electrodes is illustrated in FIG. 3A. The average bead velocity in μm/second versus distance, in millimeters (mm), from the working electrodes is shown in FIG. 3B. Error bars represent the standard deviation for each of the data points.

Figure 4:
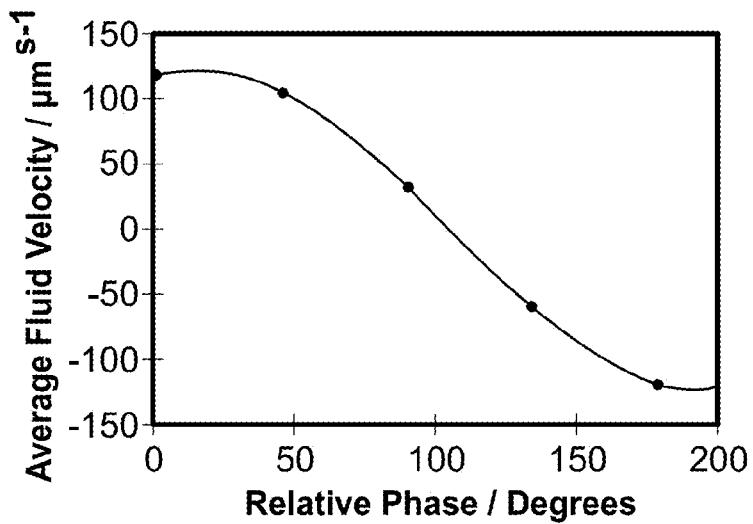
FIG. 4 is a plot of the dependence of average fluid flow velocity ($\mu m \cdot s^{-1}$) on the relative phase (°) between the sinusoidal potential waveforms applied to the electrodes and to the electromagnet.

FIG. 4 is a plot of the dependence of average fluid flow velocity ($\mu m \cdot s^{-1}$) on the relative phase (°) between the sinusoidal potential waveforms applied to the modified electrodes and to the electromagnet. The plot shows data obtained from an embodiment of the MHD microfluidic system configured as illustrated in FIG. 2A.

In other embodiments, the present invention provides a modified electrode for use with the MHD microfluidic system. A modified electrode is an electrode that includes a surface or matrix that can function as a source of charge, to provide current at the electrodes, and to affect ionic current density throughout the electrolyte between the active electrodes. The electrode can be modified to include a greater surface area, a conductive matrix accessible by the electrode to increase its double layer capacity (e.g., the conductive matrix provides an extension of the electrode's surface-area), to include an electroactive chemical species that is immobilized to the surface of the electrode and that can undergo reduction and oxidation (i.e., redox), or the electrode can include a combination of the aforementioned modifications.

Useful modified electrodes include, e.g., electrodes that have been coated with a matrix and electrodes that form composites with a matrix (e.g., an organic matrix, an inorganic matrix (e.g., metal oxide film), and combinations thereof) where the matrix does not dissolve away into the bulk fluid of the MHD system. The matrix optionally is electroactive, itself, includes electroactive chemical species (e.g., electroactive chemical species tethered to the matrix or incorporated into the matrix), or a combination thereof. Electroactive chemical species can be attached to or incorporated in the matrix through a variety of mechanisms including, e.g., blending, electrostatically, covalently, via entrapment, and combinations thereof. Examples of useful matrix compositions, some of which are intrinsically electroactive, include organometallic complexes (e.g., derivatives of polyvinylferrocene, osmium bipyridyl, and combinations thereof), conducting polymers (e.g., derivatives of polypyrrole, polythiophene, polyacetylene, and combinations thereof), xerogels, aerogels, and cryogels, that optionally include free redox-species additives (e.g., ascorbic acid, ferricyanide/ferrocyanide, ruthenium (II, III) hexaammine, mercury (I, II), iron (II, III), copper (I, II, III), lead (II), cadmium (II), zinc (II), and combinations thereof) in bulk solvent.

Other suitable matrix compositions include composites of a matrix and conductive nanoparticles (e.g., carbon nanotubes, graphitic particles, and nanoparticles (e.g., nanoparticles of different materials, e.g., gold and platinum), optionally including electroactive chemical species. One example of a useful matrix is polymerized 3,4-dioxyethylenethiophene (PEDOT).

The modified electrode is capable of generating high currents and high fluid velocities. Useful modified electrodes also exhibit a variety of other suitable properties including, e.g., having a high active surface area, electroactive chemical species highly concentrated on the electrode surface so that they do not experience the dilution effect or additional transit time caused by passing through a depleted diffusion layer to the electrode surface, and combinations thereof.

The modified electrodes provide a greater amount and higher flux of charge (i.e., ions or electrons) from redox processes, provide a greater charging capacity, and combinations thereof, relative to traditional, unmodified electrodes. The high charge capacity (coulombs) of the modified electrodes allow longer times between charging and discharging cycles of the electrodes so that relatively low cycle frequencies are possible (less than 1 kHz, or even no greater than 10 Hz) and can minimize heating.

The system can include any number of electrodes and modified electrodes having any suitable configuration including, e.g., multiband, disk and ring concentric, linear, circular, serpentine, polygonal (e.g., rectangular and triangular), solid, and outlined electrodes, and combinations thereof. The system can include multiple electrodes having different functions and operating simultaneously, sequentially, continuously, discontinuously, and combinations thereof including, e.g., a first set of electrodes that take part in a fluid pumping function while a second set of electrodes undergo regeneration.

Figures 5A, 5B:
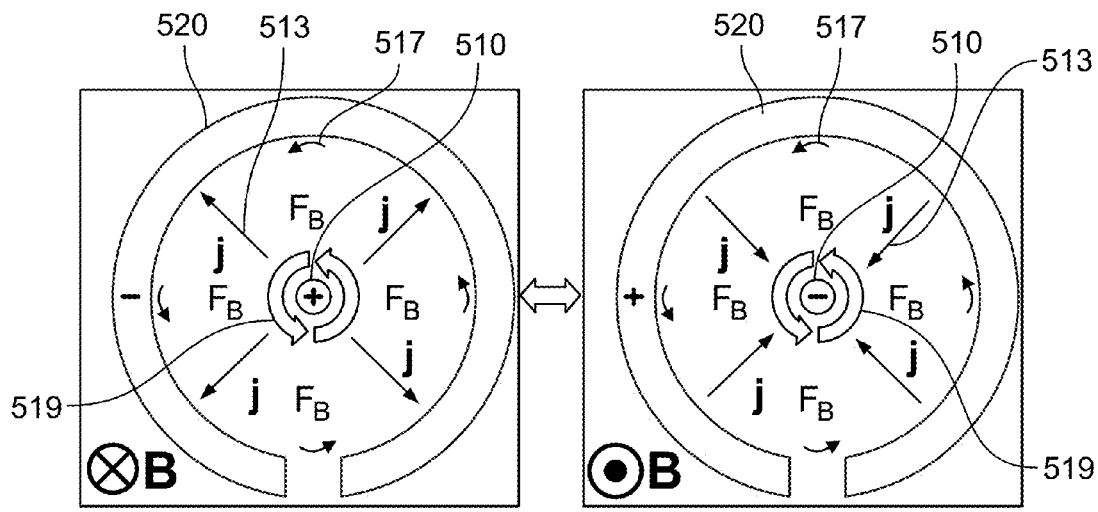
FIGS. 5A and 5B are illustrations of two other embodiments of the AC-MHD microfluidic system in which the two electrodes are in the form of a PEDOT-modified concentric disk microelectrode and a PEDOT-modified ring microelectrode.

In one embodiment, the system includes two modified electrodes in the form of a modified disk microelectrode and a modified ring microelectrode concentric with the modified disk microelectrode, as illustrated in FIGS. 5A and 5B. Useful modified concentric disk and ring microelectrodes include, e.g., conducting polymer modified microelectrodes, redox-modified microelectrodes (e.g., PEDOT-modified microelectrodes). The ionic current vector (j) (as indicated by large linear arrows 513), the magnetic field vector (B), and the direction of the MHD force ($F_B$), and therefore the direction of fluid flow (as indicated by arcuate arrows 517 and 519), are illustrated in FIGS. 5A and 5B. The velocity of the fluid flow at the center of the cell near the disk electrode 510 is greater than that at the outer perimeter of the cell near the ring electrode 520, as represented by the size and thickness of the arcuate arrows 517 and 519. Thus, velocity of the fluid flow, which is radial, decreases from electrode 510 to electrode 520.

Two different configurations are shown. In one, the negative charge is on the ring electrode and the positive charge is on the disk electrode and the magnetic field is directed away from the viewer, i.e., into the page as shown in FIG. 5A. In the other, the negative charge is on the disk electrode, the positive charge is on the ring electrode, and the magnetic field is directed toward the viewer, i.e., out of the page as shown in FIG. 5B.

Figure 6A:
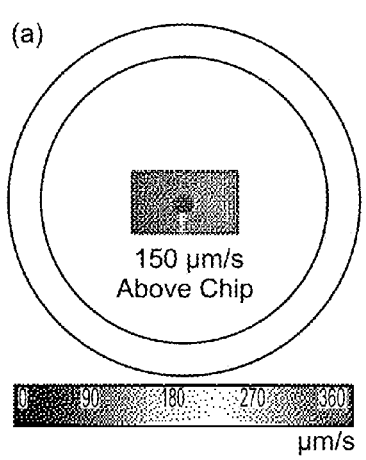
FIG. 6A is a PIV image of fluid flow recorded around the disk electrode at 150 μm above the chip.
Figure 6B:
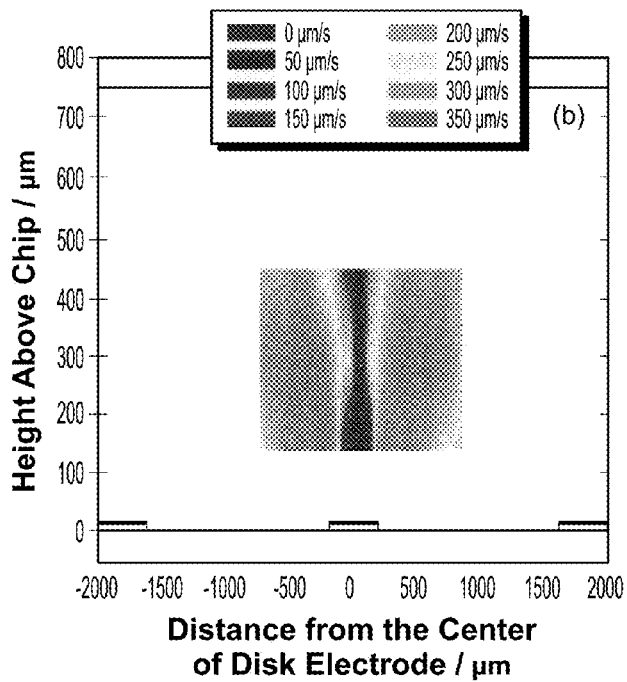
FIG. 6B is a contour plot showing flow profile around the disk electrode throughout the height of the cell of the magnetohydrodynamic microfluidic system.

A PIV image of the fluid flow recorded around the disk electrode of FIGS. 5A and 5B at 150 μm above the chip is shown in FIG. 6A. A contour plot of the flow profile around the disk electrode throughout the height of the cell is shown in FIG. 6B.

In other embodiments, electrodes 510 and 520 may be modified electrodes that are electrochemically reversible and therefore can be electrochemically regenerated (which is also referred to herein as being electrochemically recharged). The modified electrodes can be electrochemically recharged using a variety of methods including, e.g., (a) intermittent recharging and (b) alternating recharging.

Useful methods of intermittently recharging the modified electrodes include utilizing the geometric relevance of the right hand rule (i.e., $j \times B = F_B$) to allow recharging of the modified-electrodes during a static period without reversing fluid flow or producing unintentional mixing. Reversal of fluid flow can be avoided by minimizing the magnetohydrodynamic force ($F_B$) by changing the orientation of the current, the magnetic fields, or a combination thereof, or by creating forces that oppose each other. This will produce pulsed flow for a single pair of electrodes. In embodiments of the system in which there are multiple pairs of electrodes, alternating the activation of different pairs of electrodes will allow semi-continuous or continuous flow. These flow possibilities can be achieved in the presence of a constant magnetic field or a changing magnetic field.

One example of a useful method of intermittently recharging a redox-modified electrode includes redirecting the ionic current during a recharging cycle in which the absolute value of the MHD force $|F_B|$ is approximately 0, and therefore the fluid flow is approximately 0. During the recharging step, a pumping electrode's bias is reversed and paired with an oppositely-biased electrode in another location in the system, e.g., on the lid or other walls of the cell. The size and geometry of the oppositely-biased electrode can vary from smaller than the pumping electrodes to much larger than the pumping electrodes. The electrode pairing is arranged so that most of the ionic current vectors (j) are parallel to the magnetic field vectors (B), leading to $F_B=0$ and no fluid flow, i.e., fluid flow=0. Applying a reverse bias to the electrodes in sequence or simultaneously through a potential function or current function (e.g. step function) quickly recharges the modified electrodes with minimal interruption to the fluid flow. Where there are multiple pairs of pumping electrodes, different pairs of pumping electrodes can be recharged separately or simultaneously.

Another useful method of intermittently recharging the redox-modified electrodes includes redirecting the magnetohydrodynamic force ($F_B$) during the recharging cycle to make the absolute value of the MHD force $|F_B|$ nonzero in a localized place. In this method, the overall fluid flow is near 0 due to opposing flows or forces. The method optionally includes changing the orientation of the magnetic field.

Another method of intermittently recharging the redox-modified electrodes includes redirecting the MHD force ($F_B$) during a recharging cycle, where $|F_B| \neq 0$, but the net fluid flow is zero. In one embodiment, the system includes two sets of electromagnets with fields at right angles to one another. The fields are alternately turned on and off to form alternating perpendicular and parallel magnetic fields. The bias on the pumping electrodes is switched in synchrony with the changes to the magnetic fields. The synchrony occurs at the same time and includes simultaneously applying waveforms that are out of phase (e.g., waveforms applied to the electrode and the magnet that are out of phase by 90 degrees). The nonzero MHD force (FB1) component is directly above the electrodes (not in the gap) and either is small in magnitude or is directed against an opposing MHD force (FB2). For small gaps between electrodes the shear force can be large enough to prevent fluid motion.

In another embodiment, intermittently recharging modified electrodes includes changing the phase relationship between the sinusoidal wave form that is applied to the magnet to generate a magnetic field and the sinusoidal pulse that is applied to the electrodes such that the ionic current vector j and the magnetic field vector B are out of synchrony and fluid does not flow.

The redox-modified electrode can also be recharged using alternating recharging. One useful method of alternatingly recharging the redox-modified electrodes involves varying the direction of both the current and magnetic field in synchrony (or in near synchrony) so that the modified electrodes undergo charging and discharging cycles continuously and the net direction of the MHD force ($F_B$) remains essentially the same throughout the sequence. The magnetic field can be controlled by placing an electromagnet beneath the electrode (e.g., the chip on which the electrode is positioned) (B-field perpendicular to ionic current), and causing the electromagnet to generate an alternating current (AC)-magnetic field. In one embodiment, this includes passing a waveform (examples of which include a sinusoidal potential function, a sinusoidal current, a step function, and a square wave) from a first function generator through a power amplifier, which then increases the current that drives the electromagnet and causes the electromagnet to generate the AC-magnetic field. A second function generator, in synchrony with the first function generator, applies a waveform of the same frequency between two redox-modified electrodes in an environment of supporting chemical species. This creates pumping perpendicular to the ionic current vector j and the magnetic field vector B without causing reversal of flow. At the same time, relatively lower frequencies can be used so that the electromagnet can be at a higher magnetic flux density, while eddy currents and inductive heating can be avoided.

A useful conducting polymer for use with a redox-modified electrode is PEDOT (poly 3,4-ethylenedioxythiophene). This conducting polymer creates a modified electrode having greater than 1100 times the charge capacity of a bare electrode of the same geometry and a much slower response time due to the redox properties of PEDOT, which allows lower frequencies.

Other embodiments of methods of alternatingly recharging the modified electrodes include, e.g., mechanical rotation of a permanent magnet, sliding a pair of oppositely oriented permanent magnets beneath an electrode chip to flip the direction of the magnetic field without requiring an electromagnet, and combinations thereof. In other embodiments, a first MHD force ($F_B$) can be used to offset a second MHD force ($F_B$) resulting in little to no fluid flow.

Figures 7A, 7B:
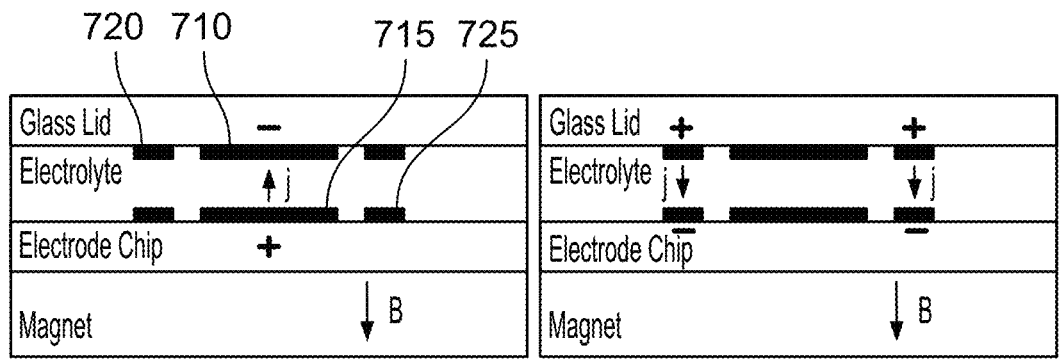
FIGS. 7A and 7B illustrate two embodiments of a method of recharging the films of modified electrodes. The methods include activating electrodes of matched geometry and opposite bias in such a way that the ionic current vector (j) is parallel to the B-field, and thus $F_B$ is approximately equal to 0 and velocity is approximately equal to 0.

FIGS. 7A and 7B illustrate embodiments concerning two methods of recharging the modified electrodes in a separate step. In this embodiment, MHD microfluidic system includes microelectrodes that are in the form of pairs of concentric disk 710 and 715 and ring 720 and 725. The modified electrode pairs include films that are disposed on the electrodes and that include immobilized electroactive species. The modified electrodes are of matched geometry and opposite bias. The method includes activating the electrodes of matched geometry and opposite bias in such a way that the ionic current vector, j, is parallel to the B-field (i.e., the magnetic field), and thus the MHD force ($F_B$) is approximately equal to 0 and velocity is approximately equal to 0.

Figures 7C, 7D:
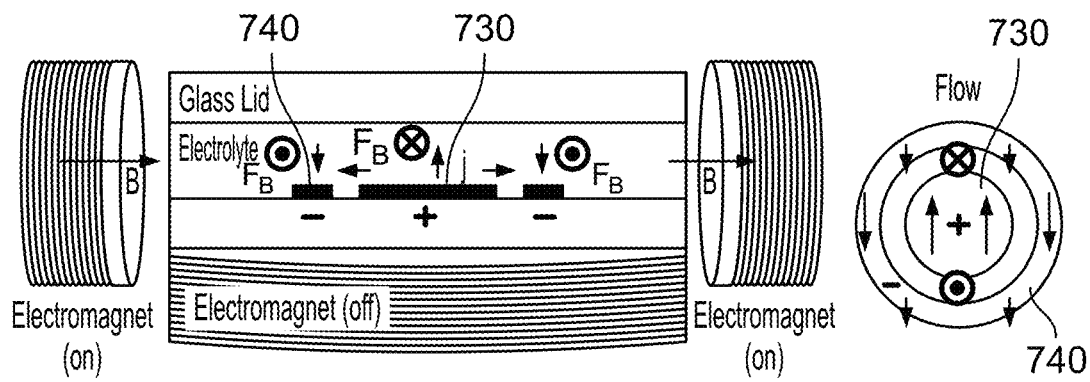
FIGS. 7C and 7D illustrate another embodiment of a method of recharging modified electrodes in which films are recharged in a separate step after switching the magnetic field such that it is parallel to the electrodes on the chip: ionic current vectors, j, that are perpendicular to the B-field produce nonzero $F_B$, because they are over the electrodes, not between them, and extend in opposite directions.

FIGS. 7C and 7D illustrate another embodiment of a method of recharging modified electrodes. In this embodiment, MHD microfluidic system includes, as the redox-modified microelectrodes, concentric disk 730 and ring 740. The films are recharged in a separate step after switching the magnetic field such that the magnetic field is parallel to the electrodes on the chip: the ionic current vectors (j) that are perpendicular to the B-field produce nonzero MHD force ($F_B$), because they are over the electrodes, not between them, and extend in opposite directions. Due to the suitable gap and electrode design, cell height, and currents, the flow vectors in FIG. 7D are tuned to cancel each other, producing a net zero fluid flow.

Figures 7E, 7F:
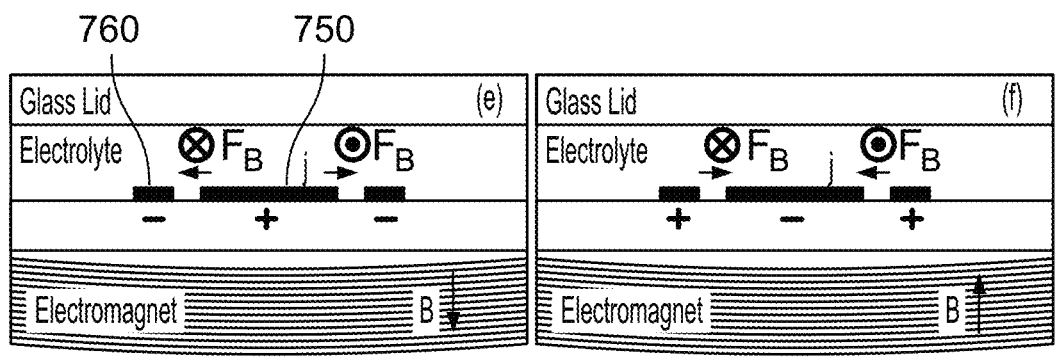
FIGS. 7E and 7F illustrate another embodiment of a method of recharging modified electrodes in which films are recharged while pumping without changing the fluid flow direction. A pulsed, fluid flow is produced by simultaneously or substantially simultaneously switching the current direction at the electrodes and the direction of the magnetic field.

FIGS. 7E and 7F illustrate another embodiment for recharging the modified electrodes in which films are recharged while pumping and without changing the fluid flow direction. In this method, a pulsed, fluid flow is produced by simultaneously or substantially simultaneously switching the current direction at the electrodes 750 and 760 and switching the direction of the magnetic field. In this embodiment, a separate recharging step is not required.

A variety of components and fluids are suitable for use in conjunction with the MHD microfluidic system. The system can include any number of magnets, electrodes and modified electrodes. Useful magnetic fields can be produced by permanent magnets, electromagnets, or a combination thereof. The magnets can be placed in different locations within the system relative to the electrodes to alter the magnetic field (e.g., the location of the magnetic field, the orientation of the magnetic field, or a combination thereof). Orientation and magnetic flux density for permanent magnets can be changed in a variety of ways including, e.g., by rotating a magnet and by placing a magnetic material, or multiple magnetic materials, in different locations. Orientation and magnetic flux density for electromagnets placed at different locations can be programmed by passing current through the electromagnet's wound wires.

Figure 8A:
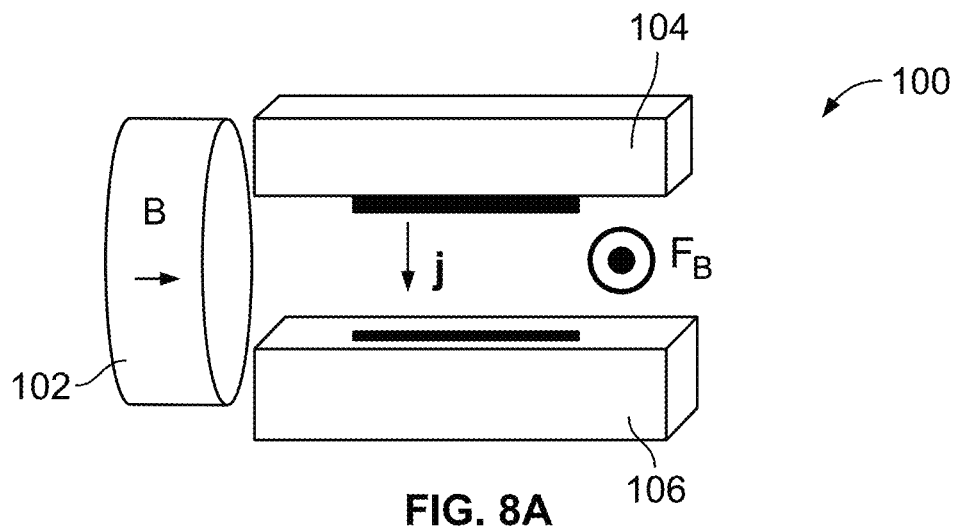
FIGS. 8A and 8B show a plan view of an embodiment of a rechargeable MHD microfluidic system that includes a movable permanent magnet.
Figure 8B:
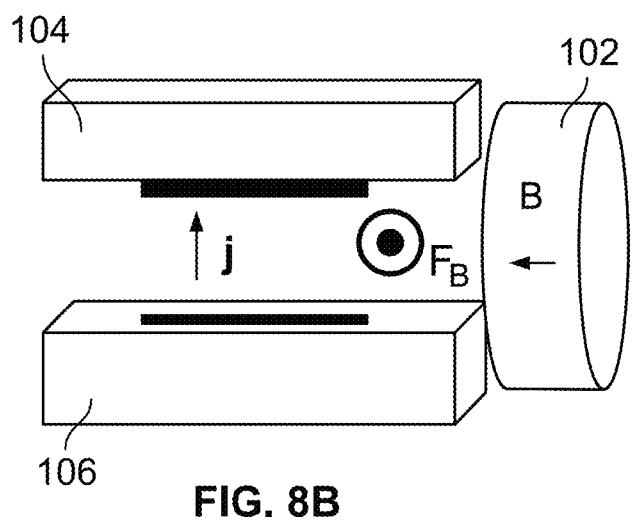

One embodiment of a rechargeable MHD microfluidic system 100 that includes a permanent magnet 102 is shown in FIGS. 8A and 8B. In a first position, permanent magnet 102 is located to the left of modified electrodes 104 and 106 such that it provides a magnetic field (B) that is perpendicular to the ionic current vector (j) produced between the first modified electrode 104 and the second modified electrode 106. Fluid flows in a direction perpendicular to both B and j as indicated by $F_B$. To recharge the modified electrodes 104 and 106, the permanent magnet 102 is moved from the first position to a second position in which it is located to the right of modified electrodes 104 and 106 as shown in FIG. 8B, and the applied electrical current or applied voltage is reversed thereby reversing the ionic current vector j. These changes cause the orientation of the magnetic field vector B and the ionic current vector j to change while maintaining the same orientation of the MHD force $F_B$ and therefore the fluid flow.

Figure 8C:
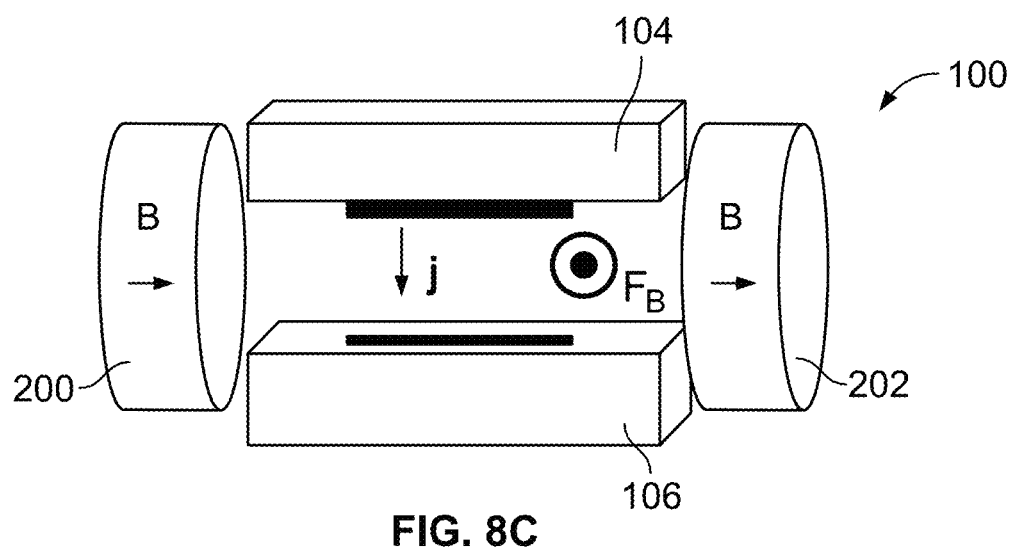
FIG. 8C shows a plan view of an embodiment of a rechargeable MHD microfluidic system.

In yet another embodiment, a pair of permanent magnets 200 and 202 may be located on the ends of electrodes 104 and 106 to provide an enhanced driving force as shown in FIG. 8C. For these embodiments, the device may be operated as described herein.

For the embodiments shown in FIGS. 8A-8C, electrodes 104, 106 or both may be replaced with multiple coplanar electrodes. Using a plurality of opposingly located electrodes, such as in the positions of electrodes 104 and 106, will further affect the flow profile vertically as well.

The fluid that includes a current carrying species can be any suitable fluid including, e.g., a liquid or a gas. Useful liquids include, e.g., water, acetonitrile, methylene chloride, tetrahydrofuran, dimethylsulfoxide, sulfur oxide, ethylenecarbonate, dimethyl formamide, diethylcarbonate, dimethylcarbonate, ionic liquids, liquid metal (e.g., mercury), and combinations thereof. Useful gases include, e.g., ion-containing gasses and plasmas. Redox reagents can also be added to the fluid as described, e.g., in U.S. Pat. No. 6,733,244, and incorporated herein, and the system optionally can be operated with the addition of solubilized electroactive chemical species in the fluid.

Useful supporting chemical species include, e.g. salts containing alkali metals (e.g., sodium chloride, potassium chloride, lithium chloride, sodium triflate, lithium perchlorate, $Li(CF_3SO_2NSO_2CF_3)$), acids (e.g., sulfuric, phosphoric, hydrochloric, hydroiodic, hydrobromic, acetic, and citric acid), buffers (e.g., Hepes, phosphate, citrate, acetate, and borate buffers), tetrabutylammonium (TBA) salts (e.g., $TBAPF_6$, $TBAClO_4$, and $TBABF_4$), molten salts (e.g., $Li_2CO_3$ and $K_2CO_3$), sodium aluminum chloride ($NaAlCl_4$), sodium chloride (NaCl), ionic liquids (e.g., $AlCl_4$- and $PF_6$— salts of 1-butyl-3-methylimidazolium), solid state materials containing ions (e.g., Nafion, conducting polymers, xerogels, aerogels, and cryogels), and combinations thereof. Other redox-species include $K_3Fe(CN)_6$/$K_4Fe(CN)_6$.

Changing the number of magnetic fields, the strength of a magnetic field, the direction of a magnetic field, and the direction of the ionic current vector (j) can be controlled by an automated system, e.g., a computer program. In addition, the MHD system can include multiple MHD subsystems. The MHD subsystems can be used to control fluid flow (e.g., direction and velocity) in multiple locations in a MHD system.

As described above, there are four main components needed to perform the MHD pumping for certain embodiments of the present invention which include: 1) at least two conductive electrodes whose potential or electronic current is controllable, 2) a fluid between the electrodes containing ions, 3) a repository of charge at the electrodes that allows conversion of electronic current to ionic current, and 4) a magnetic field that has at least one component that is perpendicular to the ionic current that is generated in the fluid. The electrodes (e.g. gold, platinum, graphite, indium tin oxide, or other conducting material) are individually addressable, and therefore can be activated, deactivated, and tuned in potential or current in a programmable fashion.

In one embodiment, the electrodes may be patterned on a silicon wafer (other insulating substrate materials are also possible) through a microfabrication process, so that the electrode shape, dimensions, number of electrodes and placement are well-controlled. Electrodes can also be formed by other means such as using wires, sheets, and meshes of conducting material.

A redox-polymer film (such as PEDOT) can be electrodeposited onto the electrodes. The electrodes could be directly constructed from a conducting polymer, instead of using electrodeposition, or they could be of a very high surface area of other conducting material so that the amount of charge is sufficient to sustain fluid flow long enough over the course of the cytometry measurement. Several chip designs can be made which allow the device to pump fluid with MHD in a programmable and controllable fashion and to be compatible with light sheet confocal microscopy.

In other embodiments, the present invention provides chip designs that may comprise one or more parallel band electrodes that provide a uniform ionic current between them, which in the presence of a perpendicular uniform magnetic field, provides a uniform flow profile in a plane, which is useful for interfacing with microscopy. Other ways of providing a net uniform MHD force in the plane in the measurement plane are possible. For example, the magnetic field can be varied across the gap between activated electrodes to offset a variation in ionic current so that the net MHD force remains uniform in the plane of the measurement.

Figure 9:
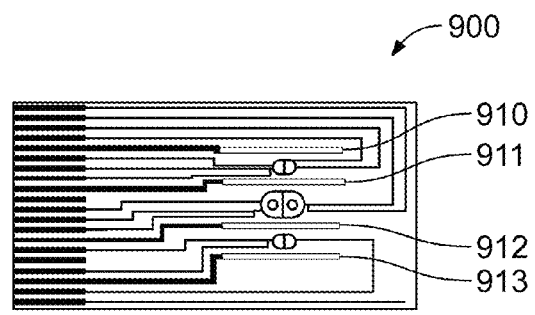
FIG. 9 illustrates a chip design of an embodiment of the present invention including four sets of long band electrodes that have been electrochemically deposited with PEDOT film.

FIG. 9 shows an embodiment of a chip 900 that may be used with the present invention. While the dimensions may vary widely, chip 900 is 2.0 inches (length)×1.0 inch (width) and contains several patterned gold features, but four long band electrodes 910-913 are provided. Each electrode may be 1.5 cm in length and 650 µm in width, and ~100 nm in thickness, with 0.3 cm gaps between the two pairs of outermost electrodes). All four electrodes can be electrodeposited with a redox film or matrix simultaneously or one by one separately, as needed. This particular electrode design has relatively wide electrodes that naturally provide more area to support more charge. To provide redundancy, the chip may be configured to consist of multiple electrodes in the event one or more electrodes become inoperable. In this embodiment, the present invention provides a chip design where there are three sets of four band electrodes. Each of the band electrodes is 2.5 cm long and 100 µm wide with 100 µm gaps between those within a set. There are larger gaps between adjacent sets (2000 µm and 5600 µm), but many variations are compatible with the light sheet microscopy.

The amount of charge (or number of coulombs) that is accessible for a cytometry experiment depends on the amount of immobilized redox species in the film or matrix. The larger the available amount of charge, the longer the cytometry measurement can be sustained in a DC mode or a slower AC frequency can be used for a given fluid velocity and geometry. There are several ways to maximize the charge during electrodeposition. One way is to increase the number of deposition cycles. Other ways include increasing the concentration of the monomer in the deposition solution, increasing the time of deposition in each cycle, and selecting a solvent/electrolyte combination that enhances the accessibility to the charge in the film through film morphology and conductivity.

The MHD pumping described above may be implemented for the chip designs described herein. Other variations include using a polymer redox-MHD having a two-electrode setup, so that there is a source of current at one and a sink of current at the other, with an ion-containing fluid between them. If using a potentiostat to control the potential, one electrode can serve as the working electrode and the other can function as a combined counter/quasi-reference electrode. A galvanostat may also be used to control the current between the two electrodes directly.

Figure 10:
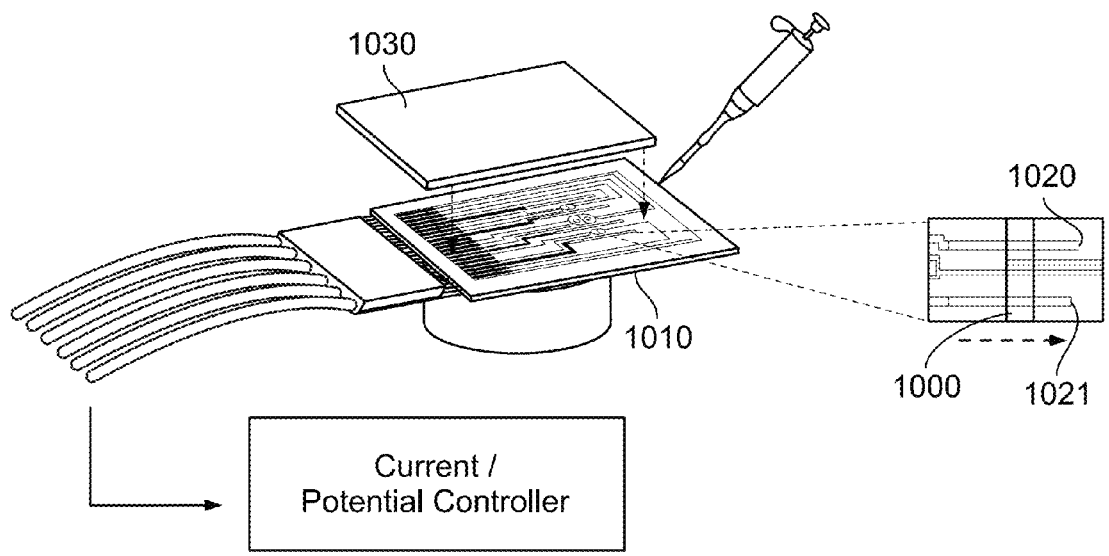
FIG. 10 illustrates another chip design of an embodiment of the present invention.
Figure 11:
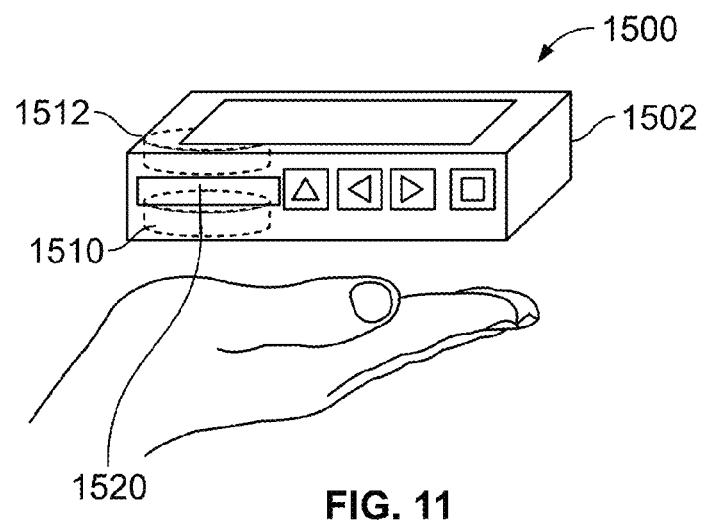
FIG. 11 illustrates a portable testing device of an embodiment of the present invention.

Simpler controllers are also possible for applying potential or current. As shown in FIG. 10, this embodiment includes chip 1000, electrode pairs 1020 and 1021, and spacer or gasket 1010 which define an opening. Spacer 1010 defines the boundaries of the fluid placed within chip 1000 and it and supports the lid, producing a closed electrochemical chamber.

In other embodiments, a poly(dimethylsiloxane) gasket 1010 with a rectangular opening is placed directly on chip 1000. The rectangular opening forms the sidewalls of the fluid chamber and leaves the film-coated electrodes exposed to the solution. About 450-500 µL of solution (with target analytes. e.g. fluorescent beads, polystyrene beads, biological cells) can be dispensed onto the chip within the polymer gasket boundary and covered with a glass coverslip 1030 (other lid materials are also possible, but if this is the entrance of the light sheet, then it needs to be transparent to the light). Then the combined assembly is placed in a magnetic field, such as placed on a permanent or electromagnet magnet. The electrical connection between chip and potential/current controller (which could be powered by a portable source of energy such as a battery) can be made via an edge connector.

In other embodiments, a concentric gold microdisk and ring electrodes may be used as active mixers for analytes as described above. Redox-containing films or matrices may also be deposited onto the ring-disk electrodes to achieve MHD pumping with rotation, and microfluidic mixing can be achieved by turning on electrodes in the presence of the magnetic field. The ability to use MHD pumping using radial flow is an added advantage of the present invention where imaging cells will be mixed with the solution and/or to perform chemical reactions, such as selective cell lysis or tagging specific cells with fluorescent labels. In between the disk and ring electrodes, there is a variation in ionic current density and thus a variable fluid flow. Fluid flow is fast close to the disk and slow at the ring electrode which generates a spiral flow, which is of interest for microfluidic mixing.

In yet other embodiments, as shown in FIGS. 11, 12 and 13A-13D, the present invention provides a compact, portable device 1500 for analyzing analytes. Housing 1502 includes a pair of magnets 1510 and 1512. In other embodiments, one magnet may be used as shown in FIGS. 13A-13B.

Housing 1502 may also include any needed electronics, optics, portable power source, and controllers. Housing 1502 also includes an opening 1520 for receiving cartridge 1550 or the components need to complete the system such as electrodes and imaging optics.

Disposable cartridge 1550 contains the electrode pumping chip and buffer solution. Cartridge 1550 is also adapted to introduce a biological sample, such as a blood sample. As shown, the magnet or magnets may be coplanar with the electrodes.

An advantage of the cartridge design is that it permits the costlier components to be integrated into the device and the less costly components to be part of the disposable cartridge. It also permits the sensors and light sources to be located within the magnets or in other locations with out interference from the magnets and other components.

Figure 12:
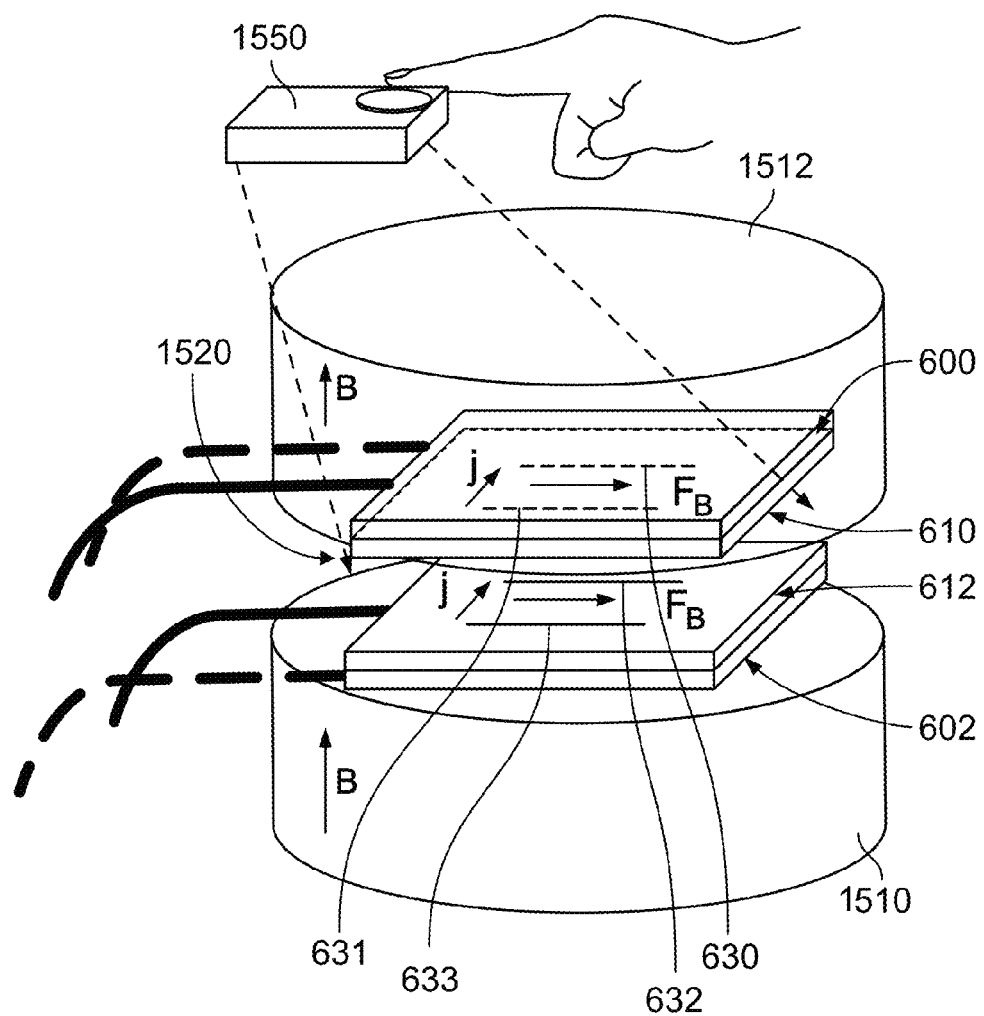
FIG. 12 illustrates an embodiment of a rechargeable MHD microfluidic system that may be used with the embodiment shown in FIG. 11.

As shown in FIG. 12, one or more waveguides 600 and 602 (or other light path, e.g. fiber optics) are provided for excitation or emission light or both. The waveguides also act as detectors.

The waveguides may also be configured to be coplanar with chips 610 and 612. As also shown, pumping electrodes 630-633 are disposed in chips 610 and 612. The coplanar arrangement of the electrodes on both floor and ceiling affect flow profile vertically, as well as horizontally. In addition, the light path for excitation and emission may be on one side or on both sides of the device between the magnets so as to avoid interference during imaging. As further shown, both waveguides 600 and 602 and chip 610 and 612 may be on one side or on both sides of the device between the magnets in a cell or opening defined by the one or magnets so as to avoid interference during imaging Magnets that may be used include one permanent magnet, or two or more permanent magnets. Electromagnets may also be used.

As shown in FIGS. 13A-13D, chips 610 and 612 contain electrodes 700-701 and 750 and 751. The electrodes may function as either a cathode or anode. In addition, a gasket 760 for containing the solution and the analyte may also be provided. The gasket may be constructed as described above.

Switching the bias of electrodes switches direction of flow 770. By reversing the bias of the anode 700 and 701 and cathode 750 and 751, the flow reverses direction and the cells can be passed repeatedly past light sheet 730. This permits the cells or analyte to be recounted and re-analyzed for averaging, extension of the experiment, and confirmation of analysis results. Another advantage of this technique is that it allows for the use of a larger chamber in which the fluid flows. Using a larger chamber reduces the pumping power needed by the device. Using a shallow chamber of about the thickness of a single cell increases fluid resistance dramatically and thereby requires additional pumping power. As stated above, the technique of switching the flow of fluid to permit recounting or reanalyzing solves this problem.

In yet other embodiments, a light sheet 730 created by a confocal microscope (not shown) may be used to analyze analytes as they pass through the chip as shown in FIGS. 13A-13D. Since fluid flow has been found to be flat between parallel band electrodes, the use of a light sheet produced by a confocal microscope is of particular usefulness.

For the embodiments shown in FIGS. 13A-13B, magnet 1510 may be replaced with a plurality of magnets arranged to replace one another in series, such as being located on a slide. In this embodiment one of the magnets has a magnetic field in direction of b, as shown, and the next magnet in the series has a magnetic field in the direction opposite the preceding magnet. In this manner, fluid flow may be reversed as well.

As further shown in FIG. 10, light sheet 1100 may be formed when a Gaussian beam is passed through a cylindrical lens (not shown) which causes rays to converge on only a single axis, yielding a two-dimensional "sheet" of light. A diffraction-limited light sheet will yield a line width (spot size) at the sample plane that is dependent on the wavelength and numerical aperture of the objective (equation 1).

$$\text{Spot Size} = \frac{1.22 \cdot \lambda}{NA} \quad (1)$$

The size of a confocal pinhole or slit aperture is determined from the product of this spot size and the objective magnification; for a 450 nm excitation wavelength and a 20× objective at 0.5 NA, the expected aperture size is 22 microns. By using the linear imaging camera in a 5-micron× 20-micron pixel binning mode, the image array itself will serve as a confocal aperture, through at reduced performance when compared to conventional point-scanning confocal methods.

Figure 16:
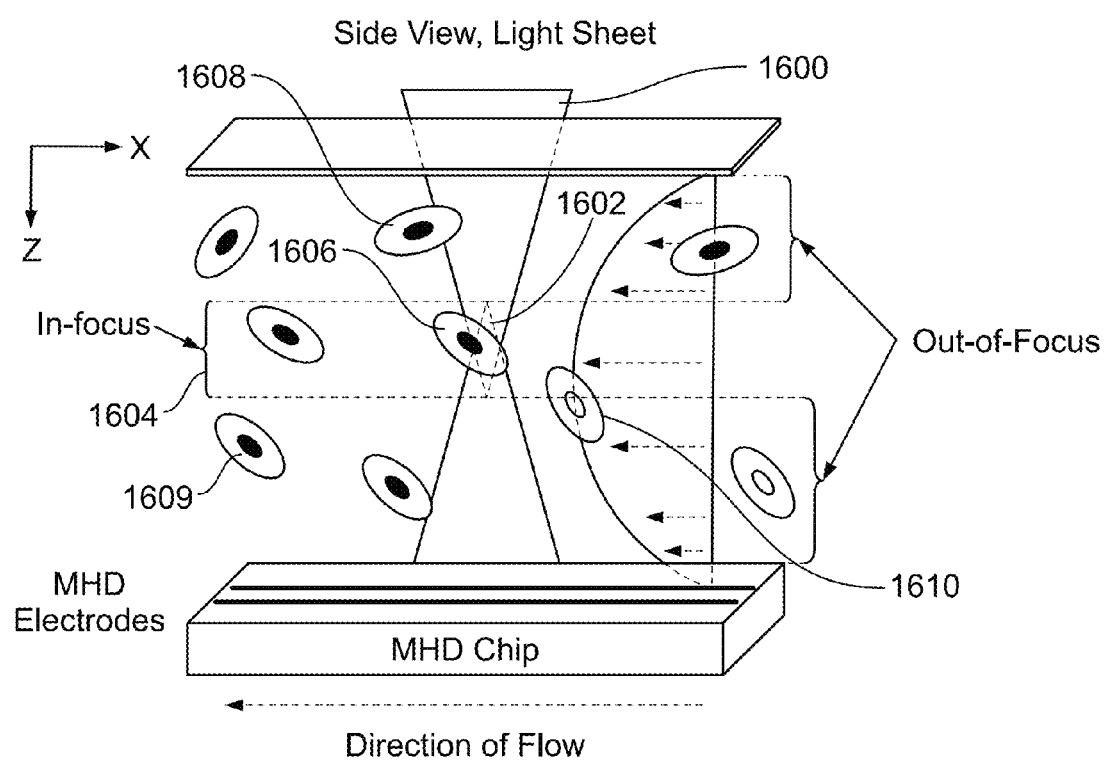
FIG. 16 depicts another embodiment of the present invention.

FIG. 16 illustrates another embodiment of the present invention. As shown, the present invention provides a light sheet 1600 that produces a 2-dimensional beam waist or convergence area 1602 at the focal plane within a chamber that contains the fluid and specimen. This illumination style provides the opportunity to selectively acquire only that which is in focal plane 1604. The light sheet is then aligned to a linear sensor in a conjugate image plane in an epitaxial configuration This allows for the system to only receive light that is transmitted from the beam waist. In addition, it allows for the chamber to be up to 2 microns in height, thereby reducing the pumping power required as compared to a chamber the height of which may be one to two cells in height.

FIG. 16 illustrates that when the beam waist illuminates a particle 1606, the particle is in focus and counted by the system. However, when other particles 1608-1610 pass above and below the waist, they are out of focus and not counted. The amount of particles counted can then be determined by the depth of focus of the waist, amount of time imaging per the speed of the particles, and density of particles in the fluid. In addition, as described above, the flow of the particles may be reversed to repass the particles past focal plane 1604 one or more times. In many situations, this repetition increases the accuracy of the system.

In other aspects, other embodiments of the present invention provide alternatives to using traditional venipuncture blood draws to obtain samples for analysis. In one embodiment of the present invention, a simple finger prick may be used to collect 40-50 μL of whole blood. The sample may then be mixed with 12 μL of 2 IU/mL Heparin in water to prevent the blood from clotting. The cells may be stained with 40-50 μL of proflavine (equal to that of the amount of whole blood drawn) at a concentration of 0.02% w/v. In using proflavine that preferentially stains nucleated cells, it was unnecessary to lyse the red blood cells. The solution at this point needs no further preparation and it sufficient to add to the syringe pump to be analyzed.

In other embodiments, the present invention provides a capillary channel flow chamber, which may be a single chamber, with the goal of transporting leukocytes in whole blood to the focal plane of a microscope. The capillary channel itself is created in a layer of PDMS (approximately 4 mm thickness) via a silicon wafer with a positive mold etched into a layer of photoresist using photolithography. This PDMS chamber is bonded to a plasma activated #2 glass coverslip to seal the channel. The channel may be 500 microns wide by 50 microns deep, extending approximately 3 centimeters in length. A micropump, such as a the MHD system described above, may be used to transport the whole blood with the stained cells through the channel. The programmable syringe pump (BS-8000120V, Braintree Scientific) enables precise control of the linear flow rate of these cells, which must be precisely controlled to eliminate motion blur in the images of rapidly moving fluid. Spherical fluorescent beads of 15-micron diameter (FluoSpheres, Life Technologies) may be used to calibrate the pump by directly measuring the speed of the beads flowing by the sensor. This measurement provides a precise correlation between the volumetric rate of the pump and the linear flow speed in the microfluidics channel.

The imaging system that may be used with the embodiment comprises an epi-illuminated fluorescent microscope consisting of an objective lens (20× air, 0.21 NA, Nikon, Japan) and a 1" 150 mm focal length tube lens coupled to an appropriate light source, optical filters, and an area scanning CMOS camera (FL3-UCM, Point Grey, Canada). Other embodiments may implement an alternative image acquisition tool, such as a Raspberry Pi microprocessor or cellphone based approach to control the camera, acquire the image and replace costly computers or laptops. The Raspberry Pi microprocessor system has rendered images, not processed by the algorithm, on a static slide. The Raspberry Pi and cell phone based system may also be used in an integrated system with cloud based computing which could be applied to low-resource point-of-care diagnostics that have little to no processing software available In addition, the present invention may also provide a system that uses computer-aided diagnostics for detection and classification of minute variations in cellular morphologic features. Image texture analysis, the analysis of statistical correlation between pixel intensities in an image, may be used to objectively analyze variations within an image that are not necessarily discernible to the human eye.

Digital images acquired by the area scan optofluidics imaging system may be used to generate a data set containing information about cellular morphology features. Image texture features are calculated in post-processing using the MATLAB Image Processing Toolbox (Mathworks, USA). These features are used to build three-part differential digital counts of leukocytes. For example, monolobar or multilobar structures in monocytes, lymphocytes, and granulocytes. Specifically, calculated features are based on statistical correlations between pixel values (such as entropy) and as well as via spatial frequency analysis or grey-level co-occurrence (GLCM) matrices. The GLCM texture analysis tool can be used to test for a variety of pixel-pair statistics across the entire single-cell image. This large pool of texture features may be tested for statistical significance between large numbers of monocyte, lymphocyte, and granulocyte images.

Data from cell populations collected by the optofluidics system may be processed cell-by-cell. To screen for features that may be useful for discriminating between the three groups of leukocytes, individual features from each dataset are averaged and analyzed for a statistically significant difference between the three groups using one-way ANOVA. Once the top-performing features are identified, they can be used to train a linear discriminant algorithm (LDA) for objective classification of unknown samples.

The linear discriminant classification algorithm may be used to calculate posterior probability, which is the probability of an unknown sample belonging to one of two or more groups. This type of algorithm must be trained using one or more of the above numerical features representing image texture, where each measurement belongs to a known group (known as groundtruths).

In other embodiments, the present invention screens large numbers of monocyte, lymphocyte, and granulocyte cells to develop a robust training dataset. This dataset may be used to initially train the LDA classifier. Subsequently, samples containing known ratios of white blood cells may be processed with the optofluidics system. The trained LDA classifier provides the selected feature values for all of the cells in the dataset, and groups each cell into the monocyte, lymphocyte, or granulocyte class. The ratio obtained via the objective LDA classifier may then be validated against the known ratio in the mixture of cell types developed by hematopathological standards.

By training the algorithm on large numbers of known monocyte, lymphocyte, and granulocyte populations, a robust objective classification scheme is developed which is observer-independent, which is ideal for the problem of screening large numbers of patients in low-resource settings.

Figure 14:
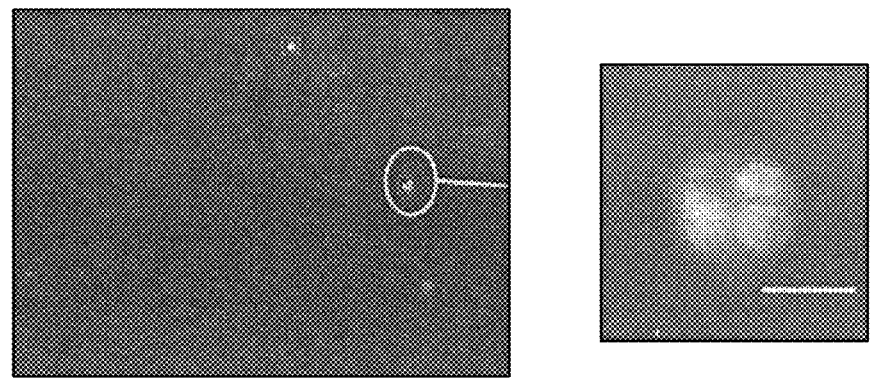
FIG. 14 provides images of blood that has been imaged using an embodiment of the present invention.

Using a conventional area-scan camera (Point Grey Flea 3) and an epi-illumination fluorescence microscope, image sets of whole blood and stained leukocytes mid-flow in a microfluidic channel were acquired as shown in FIG. 14. The leukocytes can be detected, boxed and cropped based on thresholding and size discrimination. These images are compiled into an image database to be analyzed by GLCM texture or spatial frequency analysis. Images of leukocytes may also be acquired with a similar epi-illumination fluorescence microscope and a Raspberry Pi CCD on a static slide.

Figure 15:
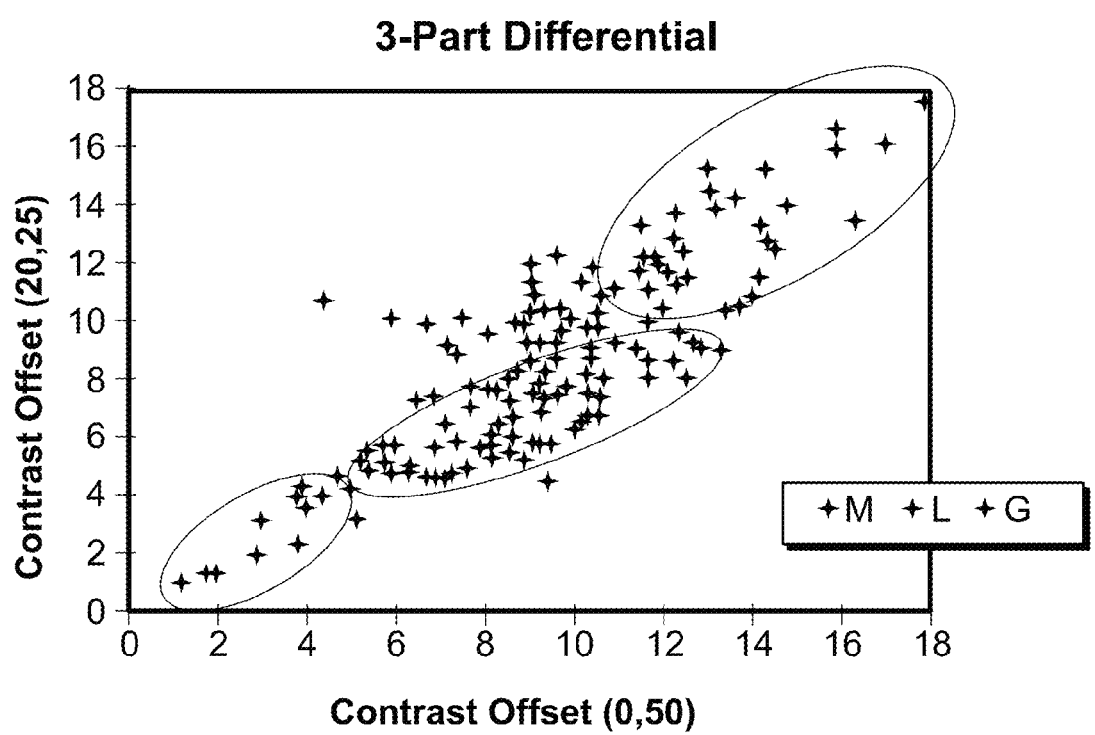
FIG. 15 illustrates a 3-part differential generated using an embodiment of the present invention.

To train the algorithm in texture analysis, pure, isolated leukocyte populations were obtained from blood samples of healthy volunteers. The images from the larger leukocyte populations were taken from pure, known populations and imaged on a static slide. The initial image texture analysis was based on pixel contrast calculation at manually determined pixel offsets and indicated a statistically significant difference as shown in FIG. 15. In other embodiments, the system may be used to classify images of cells in the channel.

While the foregoing written description enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure.

What is claimed is:

1. A microfluidic system comprising:
    a first and second electrode, said first electrode comprising at least one modified electrode comprising an immobilized electroactive chemical species;
    at least one power source adapted to create an ionic current that passes between said electrodes;
    at least one magnet adapted to create a magnetic field that is perpendicular to said ionic current;
    said system adapted receive a fluid; and
    said magnetic field and said ionic current combine to induce flow of the fluid.

2. The microfluidic system of claim 1 wherein said second electrode is a modified electrode comprising an immobilized electroactive chemical species.

3. The microfluidic system of claim 1 further comprising an opening, said first and second electrodes opposingly located in said opening and said at least one magnet located outside of said opening.

4. The microfluidic system of claim 3 further comprising:
- at least one chamber adapted to contain the fluid and said chamber adapted to receive a plurality of cells to be counted in the fluid;
- an illumination source and sensor located outside of said electrodes;
- a processor in communication with said sensor and adapted to count the cells; and
- said illumination source produces a light sheet that produces a 2-dimensional convergence area at a focal plane within said chamber, whereby the cells are counted by determining the depth of focus of said convergence area, the amount of time imaging per the speed of the cells, and the density of cells in the fluid.

5. The microfluidic system of claim 4 wherein the system is adapted to reverse the flow of the fluid containing the cells at least once to repass the cells through said focal plane.

6. The microfluidic system of claim 4 wherein said chamber is larger than a cell.

7. The microfluidic system of claim 3 further comprising:
- at least one chamber adapted to contain the fluid and said chamber adapted to receive a biological sample to be analyzed in the fluid;

an illumination source and sensor located outside of said electrodes; and a processor in communication with said sensor and adapted to analyze the biological sample.

8. The microfluidic system of claim 7 further adapted to perform a three-part differential on blood by texture analysis wherein said imaging sensor is in communication with said processor to capture an image of an illuminated blood cell;
- said processor is adapted to detect and differentiate minute variations in the morphologic features of the blood cell by texture analysis of the blood cell; and
- said illumination source produces a light sheet that produces a 2-dimensional convergence area at a focal plane within said chamber, whereby the blood cells are counted by determining the depth of focus of said convergence area, the amount of time imaging per the speed of the blood cells, and the density of blood cells in the fluid.

9. The microfluidic system of claim 1 further comprising an opening, said first and second electrodes are concentric with one another within said opening, and said at least one magnet located outside said opening.

10. The microfluidic system of claim 9 wherein said first electrode is a disk and said second electrode is a ring, said first electrode opposingly located from said second electrode and said system induces a rotational flow of the fluid that decreases from a center of the system.

11. The microfluidic system of claim 1 further including two opposingly located magnets and said electrodes located in between said magnets.

12. The microfluidic system of claim 1 further comprising maintaining fluid flow by recharging said modified electrode.

13. The microfluidic system of claim 12 wherein the recharging comprises applying at least one of a varying voltage and a varying current to said electrodes and applying a varying magnetic field.

14. The microfluidic system of claim 12 wherein the recharging comprises applying at least one of a varying voltage and a varying current to said electrodes and applying a varying magnetic field.

15. The microfluidic system of claim 12 wherein the fluid flow during recharging of the modified electrode is approximately zero.

16. The microfluidic system of claim 12 wherein the fluid flow is a pulsed fluid flow during recharging.

17. The microfluidic system of claim 12 wherein the recharging comprises
- applying at least one of a varying voltage and a varying current to the electrodes; and
- changing the direction of the magnetic field.

18. The microfluidic system of claim 1 further comprising applying at least one of a sinusoidal potential, a current waveform, and a step function to said electrodes while simultaneously altering the direction of the magnetic field.

19. The microfluidic system of claim 1 further comprising intermittently recharging the modified electrode.

20. The microfluidic system of claim 19 wherein the intermittently recharging comprises directing the flow of ionic current such that an ionic current vector, j, is in parallel with the magnetic field.

21. The microfluidic system of claim 19 wherein directing the flow of ionic current such that the ionic current vector, j, is in parallel with the magnetic field does not alter the magnetic field.

22. The microfluidic system of claim 19 wherein intermittently recharging the modified electrode comprises directing the magnetohydrodynamic force such that the absolute value of the magnetohydrodynamic force is greater than zero.

* * * * *

UNITED STATES PATENT AND TRADEMARK OFFICE
CERTIFICATE OF CORRECTION

PATENT NO. : 9,989,452 B2
APPLICATION NO. : 14/951322
DATED : June 5, 2018
INVENTOR(S) : Fritsch et al.

It is certified that error appears in the above-identified patent and that said Letters Patent is hereby corrected as shown below:

In the Specification

Column 1, Line 17: Please replace "NSF CHE0719097 and NSF CBET1336853" with -- Grant Numbers CHE0719097 and CBET1336853 --

Column 1, Line 18: Please replace "NSF." with -- National Science Foundation. --

Column 1, Line 18: Please replace "the" with -- this --

Signed and Sealed this
Third Day of December, 2019

Andrei Iancu
*Director of the United States Patent and Trademark Office*